US011033586B2

(12) United States Patent
Takahashi et al.

(10) Patent No.: US 11,033,586 B2
(45) Date of Patent: Jun. 15, 2021

(54) METHOD FOR PRODUCING RETINAL PIGMENT EPITHELIAL CELL SHEET

(71) Applicant: RIKEN, Wako (JP)

(72) Inventors: Masayo Takahashi, Wako (JP); Hiroyuki Kamao, Wako (JP)

(73) Assignee: RIKEN, Wako (JP)

( * ) Notice: Subject to any disclaimer, the term of this patent is extended or adjusted under 35 U.S.C. 154(b) by 235 days.

(21) Appl. No.: 14/423,256

(22) PCT Filed: Aug. 23, 2013

(86) PCT No.: PCT/JP2013/072589
§ 371 (c)(1),
(2) Date: Feb. 23, 2015

(87) PCT Pub. No.: WO2014/030749
PCT Pub. Date: Feb. 27, 2014

(65) Prior Publication Data
US 2015/0250828 A1 Sep. 10, 2015

(30) Foreign Application Priority Data

Aug. 24, 2012 (JP) .............................. JP2012-185932

(51) Int. Cl.
*A61K 35/44* (2015.01)
*C12N 5/071* (2010.01)
*A61L 27/38* (2006.01)
*C12N 5/079* (2010.01)

(52) U.S. Cl.
CPC .......... *A61K 35/44* (2013.01); *A61L 27/3808* (2013.01); *A61L 27/3834* (2013.01); *A61L 27/3891* (2013.01); *C12N 5/069* (2013.01); *C12N 5/0621* (2013.01); *C12N 5/0697* (2013.01); *A61L 2430/16* (2013.01); *C12N 2502/085* (2013.01); *C12N 2502/28* (2013.01); *C12N 2509/00* (2013.01); *C12N 2533/54* (2013.01)

(58) Field of Classification Search
None
See application file for complete search history.

(56) References Cited

U.S. PATENT DOCUMENTS

| 5,712,163 | A | 1/1998 | Parenteau et al. | |
|---|---|---|---|---|
| 9,902,933 | B2* | 2/2018 | Takahashi | G01N 33/5005 |
| 2006/0153815 | A1* | 7/2006 | Seyda | A61L 27/3604 424/93.7 |
| 2006/0177492 | A1 | 8/2006 | Yunoki et al. | |
| 2012/0009159 | A1* | 1/2012 | Humayun | A61K 35/30 424/93.7 |
| 2013/0108590 | A1 | 5/2013 | Takahashi et al. | |
| 2014/0057281 | A1 | 2/2014 | Takahashi et al. | |

FOREIGN PATENT DOCUMENTS

| JP | 2005261292 A1 * | 9/2005 |
| JP | 2005-261292 A | 9/2009 |
| WO | WO 2011/142364 A1 | 11/2011 |
| WO | WO 2009-127809 A1 | 10/2019 |

OTHER PUBLICATIONS

Abe et al., *Tohoku J. Exp. Med.*, 189: 295-305 (1999).
Bhatt et al., *American Journal of Ophthalmology*, 117(2): 214-221 (1994).
Carr et al., *PLoS One* 4(12), e8152 (2009).
Chung et al., *Cell Stem Cell*, 2(2): 113-117 (Feb. 2008).
Kamao et al., *ARVO Annual Meeting Abstract Search and Program Planner*, 2011: 4024 (2011).
Kamao et al., *Journal of Japanese Ophthalmological Society*, 114: 200, abstract O1-019 (2010).
Kamao et al., *Stem Cell Reports*, 2(2): 205-218 (Feb. 11, 2014).
Ke et al., *Journal of Tissue Engineering and Regenerative Medicine*, 5(2): 138-145 (2011).
Maminishkis et al., *Investigative Ophthalmology Visual Science*, 47(8): 3612-3624 (2006).
Meyer et al., *PNAS*, 106(39): 16698-16703 (2009).
Nagai et al., *Journal of Bioscience and Bioengineering*, 98(6): 493-496 (2004).
Okamoto et al., *Japanese Journal of Transplantation*, 44(3): 231-235 (2009).
Osakada et al., *Nature Biotechnology*, 26(2): 215-224 (2008).
Peyman et al., *Ophthalmic Surgery*, 22(2): 102-108 (1991).
Sheng et al., *Investigative Ophthalmol. Vis. Sci.*, 36(2): 381-390 (1995).
Sonoda et al., *Nat. Protoc.*, 4(5): 662-673 (2009).
Yaji et al., *Biomaterials*, 30(5): 797-803 (2009).
European Patent Office, Supplementary European Search Report in European Patent Application No. 12748831 (dated Oct. 3, 2014).
Japanese Patent Office, International Search Report in International Patent Application No. PCT/JP2012/054631 (dated Mar. 19, 2012).

(Continued)

*Primary Examiner* — Nghi V Nguyen

(74) *Attorney, Agent, or Firm* — Leydig, Voit & Mayer, Ltd.

(57) ABSTRACT

The present invention provides a method of producing a cell sheet comprising a retinal pigment epithelial cell layer and a vascular forming cell layer composed of stem cells having vascular formation ability or blood vessel constituting cells, comprising a step of laminating the retinal pigment epithelial cell layer and the vascular forming cell layer, and a cell sheet obtained by said method. Furthermore, the present invention provides a cell sheet for transplantation, comprising a cell layer formed with retinal pigment epithelial cells obtained by inducing differentiation of stem cells or progenitor cells ex vivo, a basement membrane secreted from said cells, and a vascular forming cell layer composed of stem cells having vascular formation ability or blood vessel constituting cells.

8 Claims, 1 Drawing Sheet

(56) References Cited

OTHER PUBLICATIONS

Cen et al., *Pediatric Research*, 63(5): 492-496 (2008).
Klimanskaya et al., *Cloning and Stem Cells*, 6(3): 217-245 (2004).
Miyazaki, *Cell Culture Convincing Q&A*, Chapter 3 ("Preparation and maintenance of incubator tool and apparatus"), Question 29 ("What is coating of dish?") and Answer (Jan. 1, 2004) English translation.
European Patent Office, Supplementary European Search Report in European Patent Application No. 13830548 (dated Mar. 2, 2016).
U.S. Appl. No. 14/001,108, filed Oct. 30, 2013.
Chinese Patent Office, First Office Action in Chinese Patent Application No. 201380051245.0 (dated Aug. 9, 2016).
Falkner-Radler et al., "Human retinal pigment epithelium (RPE) transplantation: outcome after autologous RPE-choroid sheet and RPE cell-suspension in a randomised clinical study," *Br. J. Ophthalmol.*, 95(3): 370-375 (2011).
Japanese Patent Office, International Search Report in International Patent Application No. PCT/JP2013/072589 (dated Sep. 17, 2013).
Japanese Patent Office, International Preliminary Report on Patentability in Application No. PCT/JP2013/072589 (dated Feb. 24, 2015).

\* cited by examiner

Fig. 1
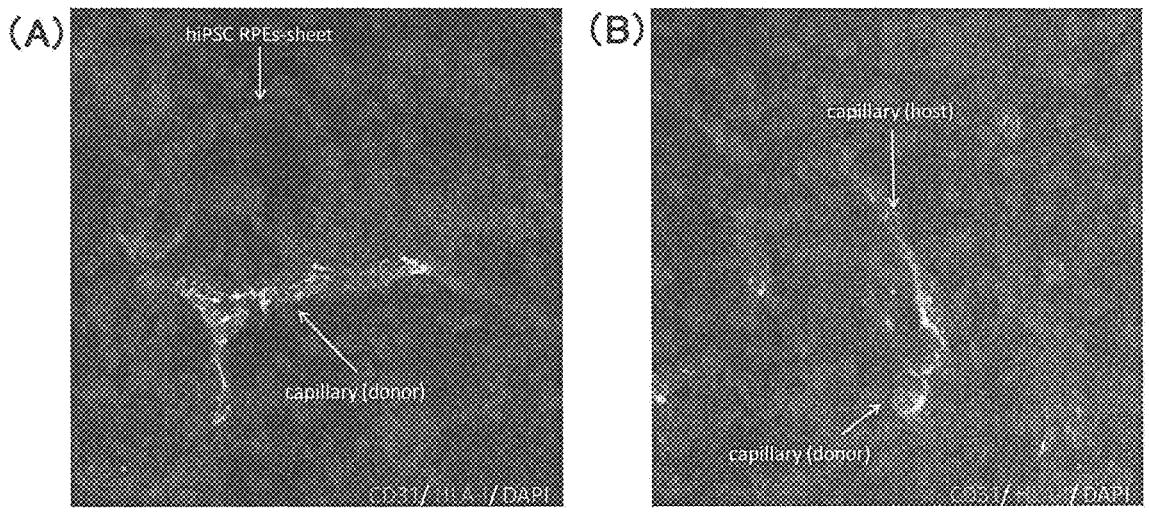
Fig. 2
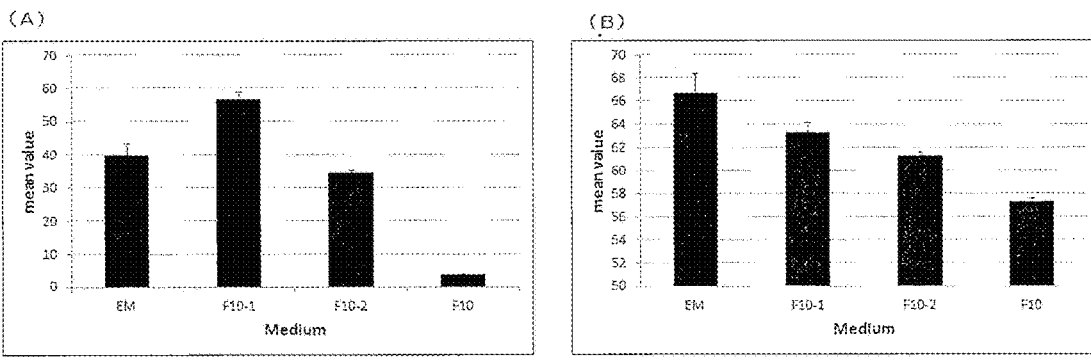
Fig. 3
253G1(iPS-RPE) (48hr)
| (ng/well) | VEGF | PEDF |
|---|---|---|
| Apical | 8.61 | 792 |
| Basal | 24.53 | 429 |
454E2(iPS-RPE) (48hr)
| (ng/well) | VEGF | PEDF |
|---|---|---|
| Apical | 1.65 | 644 |
| Basal | 14.81 | 473 |
reference: Arvydas M, IOVS.2006;47:3612-3624 (24hr)
| (ng/well) | VEGF | PEDF |
|---|---|---|
| Apical | 8.7 | 661 |
| Basal | 14.7 | 285 |

METHOD FOR PRODUCING RETINAL PIGMENT EPITHELIAL CELL SHEET

CROSS-REFERENCE TO RELATED APPLICATIONS

This patent application is the U.S. national phase of International Patent Application No. PCT/JP2013/072589, filed Aug. 23, 2013, which claims the benefit of Japanese Patent Application No. 2012-185932, filed on Aug. 24, 2012, which are incorporated by reference in their entireties herein.

TECHNICAL FIELD

The present invention relates to a production method of a cell sheet, comprising laminating a retinal pigment epithelial cell layer and a layer of cells constituting blood vessels after transplantation. The present invention also relates to a cell sheet for transplantation, comprising a cell layer formed from retinal pigment epithelial cells, a basement membrane, and a layer of cells that constitute a blood vessel after transplantation.

BACKGROUND ART

A method of treating retinal degeneration diseases by transplanting retinal pigment epithelial cells in the form of a cell sheet, which is close to in vivo form. For example, an autologous tissue transplantation including transplanting a cell sheet of retinal pigment epithelial cells cut out (as a layer accompanying choroid) from a retinal tissue of an age-related macular degeneration patient to a damaged macular area is being practiced (e.g., non-patent documents 1-3). The cell sheet derived from the patient's tissue is problematic in that an invasion risk due to an excision surgery on patient's retina, in addition to the transplant surgery, is created, the incidence rate of complication is high, the efficient rate of improvement and stable maintenance of the macular function after transplantation are low and the like.

As a method of utilizing retinal pigment, epithelial cells cultured ex vivo, without relying on collection of patient's retina, a method using a cell sheet obtained by culturing retinal pigment epithelial cells on an artificial membrane or amniotic membrane for transplantation, in order to cover a shortage of stiffness of very fragile monolayer epithelium, is known. However, artificial membranes are not suitable for transplantation since it is different from the basement membrane produced in vivo by the retinal pigment epithelial cell itself in the composition, properties, stiffness and the like, and easily induces inflammation and rejection associated therewith. In relation thereto, the present inventors reported a method of easily forming a cell sheet composed of retinal pigment epithelial cells cultured ex vivo and a basement membrane produced by the cells themselves (e.g., patent document 1 and the like). Since a cell sheet obtained by this method has a basement membrane composed of similar components as those of the living body, it is easily engrafted, has stiffness, is superior in handling property and is preferable for transplantation treatments.

Disorders of retinal pigment epithelium sometimes develop choroidal fibrillization and atrophy as complications, and deficiency of choroidal microvessels, and show unavailable supply of nutrients to retinal pigment epithelium and visual cells. Transplantation of a retinal pigment epithelial cell sheet having a basement membrane in such symptoms poses a problem that a desired treatment effect is difficult to achieve due to the absence of choroidal microvessels, which prevents sufficient supply of nutrients and oxygen to the retinal pigment epithelium after transplantation and sufficient exhibition of in vivo function of the transplanted cells.

On the other hand, as a treatment method utilizing vascular regeneration, a method including transplanting endothelial progenitor cells, forming blood vessels in vivo and treating a retinal disease is known. For example, patent document 2 reports that bone marrow-derived endothelial progenitor cells injected into the vitreous body are localized in the retinal astrocytes, vascularly incorporated to form normal retinal blood vessels. However, by the method of patent document 2 that regenerates a retinal blood vessel by utilizing localization of endothelial progenitor cells with the astrocyte, it was impossible to form a choroidal blood vessel that protects separately-located retinal pigment epithelial cells and visual cells.

DOCUMENT LIST

Patent Documents patent document 1: WO2011/142364
patent document 2: JP-A-2005-538742

Non-Patent Documents non-patent document 1: Am J Ophthalmol. 2012 January; 153(1):120-7
non-patent document 2: Acta Ophthalmol. 2011 September; 89(6):e490-5
non-patent document 3: Br J Ophthalmol. 2011 March; 95(3):370-5

SUMMARY OF THE INVENTION

Problems to be Solved by the Invention

The problem of the present invention is to develop a new method of producing a retinal pigment epithelial cell sheet conveniently and stably without using an artificial membrane, thus providing a retinal pigment epithelial cell sheet for transplantation, which shows a high engraftment rate and is superior in functionality even for patients with diseases such as chorioretinal degeneration diseases, particularly, high myopia, severe uveitis and the like associated with chorioretinal atrophy.

Means of Solving the Problems

The present inventors have conducted intensive studies and developed a production method of a cell sheet, comprising laminating a retinal pigment epithelial cell layer and cells having an ability to form blood vessel after transplantation. They have found that a cell sheet obtained by such method contains both a retinal pigment epithelial cell layer and a vascular forming cell layer, and therefore, when transplanted to a patient, it reconstructs not only retinal tissue but also choroid through vascular formation, and is useful for the treatment of chorioretinal degeneration diseases, particularly retinal degenerative diseases associated with choroidal disorders. Furthermore, when the retinal pigment epithelial cell layer was prepared by seeding retinal pigment epithelial cells on a collagen gel layer and cultivating same, the obtained retinal pigment epithelial cell layer maintained a basement membrane between the collagen gel and the retinal pigment epithelial cell sheet, had cytokine secretion ability and adhesiveness between cells similar to those of retinal pigment epithelial cells in vivo, the retinal pigment epithelial cell layer could be easily detached from the cell culture substratum by decomposing the collagen gel with collagenase, while maintaining the basement membrane. In addition, the cells constituting the retinal pigment epithelial cell layer maintained the expression of a retinal pigment epithelial cell specific marker. Based on these findings, they have conducted further studies and completed the present invention. Accordingly, the present invention provides the following:

[1] A method of producing a cell sheet comprising a retinal pigment epithelial cell layer and a vascular forming cell layer, comprising a step of laminating the retinal pigment epithelial cell layer and the vascular forming cell layer.
[2] The production method of [1], wherein the retinal pigment epithelial cell layer and the vascular forming cell layer are laminated such that the vascular forming cell layer contacts a basal surface of the retinal pigment epithelial cell layer.
[3] The production method of [1] or [2], wherein the vascular forming cell layer is composed of at least one cell selected from the group consisting of hemangioblast, vascular endothelial progenitor cell, and vascular endothelial cell.
[4] The production method of [1] or [2], wherein the vascular forming cell layer is composed of a tissue or cell derived from a patient to be transplanted with the cell sheet, or a cell derived from a donor having an HLA type matched with the patient's HLA type.
[5] The production method of any of [1]-[4], wherein the retinal pigment epithelial cell layer is a cell sheet produced by a method comprising the following steps:
(1) seeding and culturing retinal pigment epithelial cells on a collagen gel to form a cell sheet composed of the retinal pigment epithelial cells, and
(2) decomposing the collagen gel with collagenase to detach the cell sheet composed of the retinal pigment epithelial cells.
[6] The production method of any of [1]-[5], wherein the retinal pigment epithelial cell is obtained by inducing differentiation of ES cell, iPS cell or progenitor cell.
[7] A cell sheet produced by the method of any of [1]-[6].
[8] A cell sheet for transplantation, comprising a cell layer formed with retinal pigment epithelial cells obtained by inducing differentiation of stem cells or progenitor cells ex vivo, a basement membrane secreted from said cells, and a vascular forming cell layer.

Effect of the Invention

According to the present invention, it is possible to easily and stably produce a laminated sheet of retinal pigment epithelial cells, which has a vascular constituting cell layer capable of complementing a deficient choroidal blood vessel in the living body and supplying oxygen and nutrients to retina after transplantation. The cell sheet of the present invention is extremely useful, since it is superior in the engraftment rate and functionality, and can also treat severe chorioretinal degeneration diseases, for which simple retinal pigment epithelial cell transplantation cannot easily afford a sufficient treatment effect, such as chorioretinal degeneration diseases, particularly, high myopia and severe uveitis and the like, which are associated with chorioretinal atrophy.

BRIEF DESCRIPTION OF THE DRAWINGS

FIG. 1 shows immunohistochemical staining of a tissue section of a host transplanted with the cell sheet of the present invention.
FIG. 2 shows (A) a graph showing the number of vessels formed by vascular endothelial progenitor cells in each medium, and (B) a graph showing the number of vessels formed by vascular endothelial progenitor cells in each medium using matrigel.
FIG. 3 shows the results of the test of the cytokine secretion ability of the retinal pigment epithelial cell sheet.

DESCRIPTION OF EMBODIMENTS

The present invention is explained in detail in the following.
The present invention provides a method of producing a cell sheet comprising a retinal pigment epithelial cell layer and a vascular forming cell layer, comprising a step of laminating the retinal pigment epithelial cell layer and the vascular forming cell layer (the production method of the present invention).

1. Vascular Forming Cell Layer

The vascular forming cell layer in the present invention is composed of cells having vascular formation ability (vascular forming cells). When the cell sheet obtained by the production method of the present invention is transplanted into a defect site in the choroid of a retinal degeneration patient, the vascular forming cells contained in the cell sheet reconstitute a blood vessel (preferably, choroidal blood vessel) in the transplanted site, which supplies oxygen and nutrients to retinal pigment epithelial cells, and the like. Therefore, the cell sheet obtained by the production method of the present invention can exhibit a superior treatment effect by being transplanted into, particularly, a defect site in the choroid of a patient with a retinal degenerative disease associated with a choroidal defect.

While the vascular forming cell in the present invention may be a cell derived from any mammal as long as it is derived from a mammal (e.g., human, monkey, mouse, rat, dog, bovine, horse, swine, sheep, goat, cat, rabbit, hamster, guinea pig etc.), it is preferably a cell derived from human.

Examples of the vascular forming cell to be used in the present invention include hemangioblast, vascular endothelial progenitor cell, vascular endothelial cell and the like. Among these, vascular endothelial progenitor cell and the like are preferable as the vascular forming cell, since the cells are considered to be easily incorporated into the existing blood vascular network, in the process of vascular formation in vivo after transplantation. The vascular forming cell layer may contain cells other than the vascular forming cell and components other than cells, and may be composed of a cell population or tissue containing the vascular forming cells. Generally, not less than 70% (preferably not less than 80%, more preferably not less than 90%, most preferably 100%), of the cells constituting the vascular forming cell layer are vascular forming cells (preferably, vascular endothelial progenitor cells).

The vascular endothelial progenitor cell refers to a cell having an ability to differentiate into a vascular endothelial cell and committed to differentiate into a vascular endothelial cell. Plural expression patterns of cellular surface markers have been reported for vascular endothelial progenitor cell, and it is known that at least a unified definition based on the expression pattern of cell surface marker is difficult.

Examples of the expression pattern of surface marker of vascular endothelial progenitor cells reported in the past include $CD34^+$, $CD44^+$, $VEGFR2^+$ (KDR) for peripheral blood mononuclear cell-derived CD34 positive vascular endothelial cell (Science. 1997 Feb. 14; 275 (5302): 964-7); $CD31^+$, $VEGFR2^+$, $eNOs^+$, $CD105^+$, $CD34^{+/-}$, $CD133^-$, $CD45^-$, $CD14^-$, $CD117^-$ for cord blood mononuclear cell-derived vascular endothelial progenitor cell (human endothelial colony forming cell (ECFCs (registered trade mark), manufactured by Takara Bio)); and the like. While they are considered to result from the difference in the tissues from which they are derived, differentiation stage, collection method and the like, they are common in that all of them have an ability to differentiate into vascular endothelial cells. As used herein, therefore, the vascular endothelial progenitor cell is defined as "a cell having an ability to differentiate into a vascular endothelial cell, and committed to differentiate into a vascular endothelial cell", and the expression pattern of cellular surface marker tolerates the presence of plural combinations.

It is known that vascular endothelial progenitor cells are contained in yolk sac, peripheral blood, bone marrow, cord blood, mononuclear cells of these and the like, and can be prepared from these tissues or cells by a known isolation method. Examples of the isolation method include an isolation method using expression of cellular surface markers such as CD34, VEGF receptor 2 (KDR) and the like as an index and using magnetic beads and FACS; a method utilizing commercially available endothelial cell colony-forming units (CFU-ECs) (N Engl J Med. 2003; 348: 593-600) and the like. As specific examples of the production method of peripheral blood mononuclear cell- or bone marrow mononuclear cell-derived vascular endothelial progenitor cells, a method including culturing mononuclear cells separated from peripheral blood or bone marrow by a conventionally-used method in a vascular endothelial differentiation promoting medium containing cytokines such as VEGF and the like, and recovering vascular endothelial progenitor cells as adhered cells; a method of separating and recovering vascular endothelial progenitor cells, from the peripheral blood as a CD34 positive cell, which have been recruited from bone marrow by using G-CSF (Yakugaku Zasshi 2007 125(5) 841-845 etc.) and the like are known.

In addition, differentiation of the vascular endothelial progenitor cell from various cells can be induced. For example, a method of inducing differentiation from fibroblast through dedifferentiation; a method of inducing differentiation of pluripotent stem cell such as ES cell, iPS cell and the like into vascular endothelial progenitor cell (WO 2008/056779, WO 2009/035217 and the like) and the like are known. These vascular endothelial progenitor cells can be used alone or plural kinds thereof can be used in combination. As the vascular endothelial progenitor cell in the present invention, a cell mixture containing other cells can be used. For example, bone marrow cells, peripheral blood mononuclear cell, bone marrow mononuclear cell and the like containing vascular endothelial progenitor cell can also be used directly.

Vascular endothelial cells can be prepared by a known method such as a method including separating the cells from a vascular tissue in the living body by using expression of a cellular surface marker such as CD31 and the like as an index and using magnetic beads and FACS; a method of inducing differentiation by culturing the above-mentioned vascular endothelial progenitor cell in the presence of an inducer such as VEGF and the like, and the like. In addition, differentiation of various cells into the vascular endothelial cells can also be induced, and it is known, for example, differentiation into the vascular endothelial cells can be induced from somatic stem cells such as mesenchymal stem cells, adipose tissue derived-stem cells and the like; progenitor cells such as cardiac muscle progenitor cells, neuronal precursor cells and the like; pluripotent stem cells such as ES cells, iPS cells and the like; and the like. Furthermore, as a commercially available product of vascular endothelial cells, human microvascular endothelial cells (HMVEC), human umbilical cord vascular endothelial cells (HUVEC), human aortic endothelial cells (HAEC, HAOEC) and the like can be obtained.

Hemangioblast is a common ancestor cell of vascular endothelial progenitor cell and hematopoietic stem cell, and can be prepared from a vascular tissue in the living body by using expression of cellular surface marker such as CD133, CD144, CD45 and the like as an index by a known method such as a separation method using magnetic beads and FACS and the like. As expression patterns of cellular surface marker of hemangioblast, for example, a combination of $CD133^+$, $CD144^+$, $CD45^+$, $CD34^+$, $VEGFR2^+$, $CD31^-$ has been reported (Stem Cells Dev. 2004 June; 13(3):229-42.).

As the vascular forming cell to be used in the present invention, a tissue or cell derived from a patient to be transplanted with the cell sheet obtained by the production method of the present invention, or a cell derived from a donor having HLA type matched with the patient's HLA type and the like can be utilized. As the vascular forming cell to be used in the present invention, a vascular endothelial progenitor cell is particularly preferable.

As a vascular forming cell preferable for autologous transplantation use, for example, a patient's tissue, a cell collected therefrom, and a cell derived from iPS cell established from patient's somatic cell (patient's iPS cell) are preferably used, since a burden on the patient is small. Being less invasive, patient's peripheral blood, a mononuclear cell collected therefrom, a cell derived from patient's peripheral blood mononuclear cell, a cell derived from patient's iPS cell and the like are preferably used. These can be prepared using a cell derived from the patient by the aforementioned method.

As a vascular forming cell preferable for allotransplantation, for example, a cell derived from a donor having HLA type matched with the patient's HLA type is preferably used to suppress rejection. The cell derived from a donor having HLA type matched with the patient's HLA type includes a donor tissue matching the patient's HLA type, a cell collected therefrom, cells derived from iPS cell established from donor having HLA type matched with the patient's HLA type (HLA-matched donor iPS cell) and the like. The tissue and cell with matched HLA type can also be obtained from bone marrow bank, cell bank and the like. In particular, a cell having 3 locus (HLA-A, HLA-B, HLA-DR) homozygous showing low rejection with other HLA types is preferable as a donor cell since it matches with many patients' HLA types.

The vascular forming cell layer is preferably laminated on the retinal pigment epithelial cell layer such that the vascular forming cell layer contacts a basal surface of the retinal pigment epithelial cell layer. The vascular forming cell layer only needs to be laminated on at least one part of the retinal pigment epithelial cell layer. The density of the vascular forming cells relative to the retinal pigment epithelial cell layer is not particularly limited, and can be determined as appropriate in consideration of the choroidal disorder state in the transplanted site, affinity for existing blood vascular network and the like. The density of the vascular forming cell relative to the retinal pigment epithelial cell layer is, for example, about $1\times10^2$-$1\times10^6$ cells/cm$^2$, preferably about $1\times10^3$-$1\times10^5$ cells/cm$^2$, since vascular forming cells are easily incorporated into the existing blood vessels in the living body when the density of the vascular forming cells is low. When transplantation into a patient with large damage on choroid and markedly small number of remaining blood vessels is desired, a vascular forming cell layer having a high density of the vascular forming cells is preferable.

As a step of laminating a retinal pigment epithelial cell layer and a vascular forming cell layer (laminating step), a known method can be utilized as a method of laminating plural cell layers. Examples of such method include a method of laminating plural sheet-like cell layers, a method including seeding cells which constitute one cell layer, on the other sheet-like cell layer, a method including placing one sheet-like cell layer on the other cell layer cultured in a culture container, a method including seeding cells which constitute one cell layer, on the other cell layer cultured in a culture container and the like. In the present invention, it is preferable to laminate two cell layers such that the vascular forming cell layer contacts a basal surface of the retinal pigment epithelial cell layer. For example, a sheet-like retinal pigment epithelial cell layer is placed on a vascular forming cell layer cultured in a culture container, whereby the vascular forming cell layer contacts a basal surface of the retinal pigment epithelial cell layer. A cell sheet obtained by laminating layers in a culture container can be directly put to use.

In a preferable embodiment of the laminating step in the present invention, vascular forming cells are seeded using a medium in a culture container and cultured to form a vascular forming cell layer in the culture container, a retinal pigment epithelial cell sheet formed separately is placed on the vascular forming cell layer, and the medium is aspirated, whereby the both cell layers are laminated such that the vascular forming cell layer contacts a basal surface of the retinal pigment epithelial cell layer. The aforementioned medium is not particularly limited as long as it is a composition capable of maintenance culture of vascular forming cells and retinal pigment epithelial cells. Generally, both a medium for vascular forming cell culture and a medium for vascular endothelial progenitor cell culture can be used. For example, as a medium for vascular endothelial progenitor cell culture, commercially available products such as EGM-2 medium (manufactured by Takara Bio) and the like can be used. After seeding of vascular forming cells, it is preferable to stand the cells for at least the time necessary for the cells to adhere to the surface of the culture container and form a vascular forming cell layer (e.g., about 10 hr-24 hr) and, where necessary, a culture period of about 1 day-3 days may be set to achieve growth to reach a desired cell number.

The production method of the present invention may further contain a step of recovering a cell sheet wherein a retinal pigment epithelial cell layer and a vascular forming cell layer are laminated (recovery step). A method of recovering the cell sheet is not particularly limited as long as it can recover the sheet while maintaining the sheet structure, and a known method can be used. Examples of such method include a method of detaching a cell sheet from a culture container by an enzyme treatment, a method using a cell non-adhesive culture container, a method including laminating cell layers by using a culture container surface-treated to be cell-adhesive, and detaching the formed cell sheet by treating with an enzyme etc., and the like. In the present invention, when vascular forming cells adhere to a surface of a culture container and fixed in the laminating step, the retinal pigment epithelial cell layer is easily laminated on the vascular forming cell layer. Therefore, a method including laminating cell layers by using a culture container surface-treated to be cell-adhesive and detaching the formed cell sheet from the culture container is preferable. In one embodiment, a cell sheet is formed in a culture container surface-treated with a temperature-responsive polymer, and the cell sheet is detached by a treatment of the temperature change. The temperature-responsive polymer refers to a polymer having a hydration force that changes in a temperature-dependent manner and, for example, a temperature-responsive polymer having a hydration force that changes in a temperature range of 0-80° C. is described in JP-A-2-211865. To be specific, for example, it can be obtained by homopolymerization or copolymerization of the following monomers. Examples of the usable monomer include (meth)acrylamide compound, N-(or N,N-di)alkyl substituted (meth)acrylamide derivative, and vinylether derivative. In the case of a copolymer, any two or more kinds of these can be used. Furthermore, monomers other than the above-mentioned monomers, copolymerization with ionic monomer to improve adhesiveness and growth of cells, graft or copolymerization of polymers, or a mixture of polymer and copolymer may be used. The temperature-responsive polymer undergoes hydration and dehydration in response to temperature change, and the temperature range thereof is 0° C.-80° C., preferably 10° C.-50° C., more preferably 20° C.-45° C. A preferable temperature-responsive polymer is, for example, poly(N-isopropylacrylamide). Poly(N-isopropylacrylamide) is a polymer having a lower critical solution temperature of 31° C. When it is in a free form, it undergoes dehydration in water at not less than 31° C., at which the polymer chain coagulates and the polymer is clouded. Conversely, at a temperature of less than 31° C., the polymer chain is hydrated and the polymer is dissolved in water. When poly(N-isopropylacrylamide) is fixed on the surface of a culture container, poly(N-isopropylacrylamide) is dehydrated at not less than 31° C., and the surface of the culture container acquires hydrophobicity and shows adhesiveness to cells (e.g., vascular forming cell, retinal pigment epithelial cell). At a temperature of less than 31° C., poly(N-isopropylacrylamide) is hydrated, and the surface of the culture container acquires hydrophilicity and shows non-adhesiveness to cells. Utilizing such temperature responsiveness, cells are cultured at a temperature (e.g., 37° C.) not less than the lower critical solution temperature (31° C. for poly(N-isopropylacrylamide)) in the laminating step to achieve adhesion of the cell sheet to the culture container, a temperature less than the lower critical solution temperature (e.g., 20° C.) is provided in the recovery step to enable detachment and isolation of the cell sheet from the culture container without applying an enzyme treatment. Culture containers coated with such temperature-responsive polymer are described in JP-A-2-211865, JP-A-05-192138, JP-A-2008-220354 and the like. In addition, such culture container is commercially available as a temperature-sensitive culture container (manufactured by Cellseed, UpCell (registered trade mark)). Vascular forming cells seeded in a culture container are preferably adhered onto the culture container so that they will be certainly transferred to the retinal pigment epithelial cell layer.

In a preferable embodiment, vascular forming cells are adhesion-cultured in a temperature responsive culture container coated with poly(N-isopropylacrylamide) at a temperature (e.g., 37° C.) not less than the lower critical solution temperature (31° C.) to form a vascular forming cell layer. Then, a separately-prepared retinal pigment epithelial cell layer (retinal pigment epithelial cell sheet) is laminated on the vascular forming cell layer while maintaining a temperature (e.g., 37° C.) not less than the lower critical solution temperature, such that the vascular forming cell layer contacts a basal surface of the retinal pigment epithelial cell layer. After incubation at a temperature (e.g., 37° C.) not less than the lower critical solution temperature for a time sufficient for the vascular forming cell layer and the retinal pigment epithelial cell layer to be adhered to each other, the culture is cooled to a temperature (e.g., 20° C.) less than the lower critical solution temperature, whereby the formed cell sheet is detached from the culture container. Cooling and detachment are performed, for example, by aspirating the medium, adding a medium with a temperature (e.g., 20° C.) less than the lower critical solution temperature to the culture container, standing same for a time necessary for detaching the cell sheet from the culture container (e.g., not less than 30 min), and recovering the laminated cell sheet. The medium is the same as those recited as examples in the preferable embodiment of the laminating step. When the standing time after addition of the cooling medium is too long, detachment of the cell sheet becomes difficult. Thus, it is preferable to recover the sheet within one day from the addition of the medium.

The production method of the present invention may also comprise a step of applying a vascular formation treatment to the vascular forming cell layer. The vascular formation treatment step may be a pre-step or a subsequent step of the step of laminating a retinal pigment epithelial cell layer and a vascular forming cell layer. The vascular formation treatment can be performed by a known method and, for example, a known method of inducing tube formation such as a method of culturing vascular forming cells in a collagen gel in the presence of a factor such as VEGF, IGF-1, PDGF and the like, a method of contacting a vascular forming cell layer with matrigel and the like can be applied. Since retinal pigment epithelial cell secretes VEGF, the supernatant of retinal pigment epithelial cell culture can also be used for vascular formation.

When a vascular formation treatment is applied, all vascular forming cells constituting the vascular forming cell layer may have a vascular structure, or only a part thereof may have a vascular structure. In the vascular forming cell layer, it is desirable to constitute a blood vessel having a structure suitable for the environment of the transplantation site in vivo. For example, when the cell sheet obtained by the production method of the present invention is transplanted without any vascular formation treatment ex vivo and without a vascular structure, transplanted vascular forming cells spontaneously form a blood vessel in vivo, during which process the blood vessel is linked to existing blood vessels to easily form a functional blood vascular network. On the other hand, when the damage on choroid is large and the remaining blood vessels are markedly small in number, reconstruction of a blood vascular network based on the transplanted vascular structure can be preferably promoted by applying the vascular formation treatment to the vascular forming cell layer.

The vascular forming cell layer may contain one or plural kinds of cells other than the vascular forming cells, for example, cells supporting vascular formation or angiogenesis such as hematopoietic stem cell and the like, blood vessel constituting cells other than the vascular endothelial cell such as vascular smooth muscle cell, blood cell and the like, and the like. The vascular forming cell layer may further contain components other than cell, for example, a factor promoting angiogenesis, and the like.

2. Retinal Pigment Epithelial Cell Layer

The retinal pigment epithelial cell to be used in the present invention may be a primary cell directly collected from an eyeball, or a cell after several passages. The primary retinal pigment epithelial cells can be isolated by a known method. For example, in the case of eyeball-derived retinal pigment epithelial cells, a cadaveric eyeball is isolated, rapidly divided at the equatorial segment, the vitreous body and the retina are removed and treated with collagenase, hyaluronidase and the like as necessary, the cells are collected by scratching with a cell scraper, or treatment with trypsin or EDTA solution to liberate the cells from the Bruch's membrane, stood in a culture medium to induce adhesion to the culture dish and growth, and the cells grown in the required number are appropriately passaged with a trypsin treatment etc. to sufficiently secure the cell number.

Furthermore, these cells may also be the cells obtained by inducing differentiation of undifferentiated pluripotent stem cells such as embryonic stem cell (ES cell), induced pluripotent stem cell (iPS cell) and the like, stem cells including somatic stem cells such as neural stem cell and the like, or progenitor cells including neural progenitor cell and retinal progenitor cell. The ES cell may also be an ES cell produced by nuclear reprogramming of a somatic cell. In addition, as the stem cell, the object cell may be prepared by inducing differentiation of induced pluripotent stem cell (iPS cell) reported in recent years. The iPS cell is a somatic cell-derived induced stem cell having properties equivalent to those of ES cell, which can be produced by introducing a particular nuclear reprogramming substance (nucleic acid, protein, low-molecular-weight compound etc.) into a somatic cell [Takahashi, K. and Yamanaka, S., Cell, 126: 663-676 (2006); Takahashi, K. et al., Cell, 131: 861-872 (2007)]. The conditions and medium used for differentiation of the aforementioned stem cell into the object differentiated cell may follow conventionally-known conditions and medium, or may be appropriately determined by those of ordinary skill in the art. In the present invention, a cell obtained by inducing differentiation of stem cell or progenitor cell, preferably pluripotent stem cell, is preferably used as the retinal pigment epithelial cell to be used for cell sheet, since a retinal pigment epithelial cell at an appropriate maturation stage can be prepared, and particularly, comparatively immature retinal pigment epithelial cells can be prepared and a cell sheet can be advantageously formed. In addition, when the cell sheet to be produced by the present invention is for transplantation, use of an iPS cell is preferable since a cell sheet obtained using a somatic cell of the subject, who receives transplantation, as a source of iPS cell does not have antigenicity against the subject. When a stem cell is induced to differentiate, for example, human ES cell or pluripotent stem cell such as iPS cell and the like is cultured in an ES cell differentiation medium added with Wnt antagonist such as Dkk-1, CKI-7 and the like and Nodal antagonist such as Lefty A, SB-431542 and the like. When cultured for a given period, Rx, Pax6 and Mitf, which are retinal progenitor cell markers, are expressed, and human retinal pigment epithelial cells can be obtained by morphological observation with an optical microscope, by confirming cells having a polygonal form and pigment [Neuroscience Letters 2009 Jul. 24 458(3) 126-31, Journal of Cell Science 2009 Sep. 1 122(Pt 17) 3169-79].

The retinal pigment epithelial cell layer in the present invention is composed of a layer of retinal pigment epithelial cells arranged on a flat plane and, for example, can be composed as a cell sheet comprising retinal pigment epithelial cells produced by a known method. As a production method of such cell sheet (retinal pigment epithelial cell layer), for example, the method described in WO 2011/142364 is known.

A preferable embodiment of the cell sheet of the present invention is a cell sheet wherein the retinal pigment epithelial cell layer is produced by a method including the following steps (hereinafter to be referred to as "the collagen method"):
(1) seeding and culturing retinal pigment epithelial cells on a collagen gel to form a cell sheet composed of the retinal pigment epithelial cells, and
(2) decomposing the collagen gel with collagenase to detach the cell sheet composed of the retinal pigment epithelial cells.

While the retinal pigment epithelial cell to be seeded in step (1) may be a cell derived from any mammal as long as it is derived from a mammal (e.g., human, monkey, mouse, rat, dog, bovine, horse, swine, sheep, goat, cat, rabbit, hamster, guinea pig etc.), it is preferably a cell derived from human.

In the collagen method, the retinal pigment epithelial cells are cultured by seeding on a collagen gel. The collagen used for the collagen gel may be any as long as it is derived from a mammal (e.g., human, monkey, mouse, rat, dog, bovine, horse, swine, sheep, goat, cat, rabbit, hamster, guinea pig etc.) and, for example, human- or swine-derived collagen is used. Examples of the tissue from which collagen is derived include tendon, skin and the like. While the kind of the collagen may be any, one other than the collagen constituting the human basement membrane is preferable, one other than type-IV collagen is specifically preferable. Of these, type I collagen is preferably used. While a collagen gel can be produced by, for example, a conventionally-known production method, in the present invention, a gel composed of a collagen fiber network is produced by inducing fibrogenesis of collagen, as described in the below-mentioned Example. Since the fibrotic collagen has strength and flexibility in combination, it is easy to handle, shows good maintenance of cell proliferation and cell differentiation, and is preferable as the collagen gel to be used in the present invention. In addition, the collagen to be used in the present invention is required to maintain cells, which are seeded on the collagen gel, on the gel surface without allowing them to sink into the gel layer. As the collagen, therefore, preferred is one wherein the gel has the strength necessary for cell proliferation and, for example, collagen having a large amount of intermolecular crosslinking is preferable. As such collagen, tendon-derived collagen can be mentioned.

While the collagen concentration of the aforementioned collagen gel may be in any range as long as it can afford a gel having strength permitting engraftment and growth of retinal pigment epithelial cells, and satisfying solubility facilitating decomposition by collagenase, viscosity enabling easy handling and the like, it is preferably 0.1% (W/V)-0.5% (W/V), more preferably 0.2% (W/V)-0.3% (W/V). When the collagen concentration of the collagen gel is less than 0.1% (W/V), the strength of the collagen gel becomes insufficient, and therefore, the colonization rate and cell proliferation rate of retinal pigment epithelial cells decrease. When the collagen concentration of the collagen gel exceeds 0.5% (W/V), the time of a collagenase treatment to decompose the collagen gel becomes long, which is feared to exert an adverse influence on the cells.

While the volume of a collagen gel mixed solution used for the production of the aforementioned collagen gel varies depending on the culture area and shape of a culture substratum to be used for the cell culture, it is preferably about 100 µl-about 250 µl, more preferably about 150 µl-about 200 µl, per unit area ($cm^2$). When the amount of the collagen gel mixed solution is too small, a collagen gel layer having a thin center part due to the influence of a surface tension applied to the gel surface is formed, and the sheet tends to be damaged during cutting out of the cell sheet composed of the retinal pigment epithelial cells, since the cells directly contact with a culture substratum for when the retinal pigment epithelial cells are cultured. When the amount of the collagen gel mixed solution is in excess, a thick collagen gel layer is formed on a culture substratum, which relatively reduces the amount of the culture medium, and therefore, maintenance culture is not easy to perform, collagenase treatment takes time, and damages on the cell sheet composed of the retinal pigment epithelial cells are feared.

In step (1), a cell sheet composed of the retinal pigment epithelial cells can be produced by seeding and culturing the aforementioned retinal pigment epithelial cells on the collagen gel of a cell culture substratum. The cell culture substratum in the present invention is not particularly limited as long as it is for cell culture. Examples thereof include culture containers having a porous membrane such as transwell and the like, flask, tissue culture flask, dish, petri dish, tissue culture dish, multi dish, microplate, microwell plate, multiplate, multiwell plate, chamber slide, petri dish, tube, tray, culture bag and roller bottle. Culture containers having a porous membrane are preferable, since a collagenase treatment and a cutting operation of the cell sheet are conveniently performed. For example, a commercially available transwell is preferably used. Examples of the material of the cell culture substratum in the present specification include, but are not limited to, inorganic materials such as metal, glass, ceramic, silicon and the like, organic materials represented by elastomer, plastic (e.g., polyester resin, polyethylene resin, polypropylene resin, ABS resin, nylon, acrylic resin, fluororesin, polycarbonate resin, polyurethane resin, methylpentene resin, phenol resin, melamine resin, epoxy resin, vinyl chloride resin).

The number of the retinal pigment epithelial cells to be seeded may be in any range as long as it is a cell density capable of forming a cell sheet. However, when the cell density is too low, the cell shape is bad, the culture time before reaching confluence is long, and further, the time necessary for cell maturation and coloring is long. When the cell density is too high, similarly, cell proliferation is suppressed, the culture time before reaching confluence tends to be long, and the cells may die from being overcrowded. Therefore, the density of the cells to be seeded is preferably about $4.5 \times 10^4$ cells/$cm^2$-about $8.5 \times 10^5$ cells/$cm^2$, more preferably about $8.5 \times 10^4$ cells/$cm^2$-about $8.5 \times 10^5$ cells/$cm^2$, most preferably about $4.5 \times 10^5$ cells/$cm^2$.

A monolayer cell population (cell sheet) composed of retinal pigment epithelial cells can be formed by culturing the retinal pigment epithelial cells seeded on collagen gel in a culture medium. A culture medium can be used without particular limitation as long as it is a cell culture medium generally used in the pertinent field. For example, basal media described in "Japan tissue culture conference ed., Technique of Tissue Culture 3rd edition" page 581, published by Asakura Shoten, such as F-10 medium, F12 medium, MEM, BME medium, DMEM, αMEM, IMD medium, ES medium, DM-160 medium, Fisher medium, WE medium, RPMI1640 medium and the like, can be used. Furthermore, serum (fetal bovine serum etc.), various growth factors (EGF, FGF, HGF, PDGF etc.), antibiotic, amino acid and the like may be added to the basal medium. The pH of the medium is preferably about 6-about 8. As for culture, for example, a primary culture is performed generally at about 30-about 40° C. for about 15-about 60 hr until the retinal pigment epithelial cells become confluent. Thereafter, a secondary culture is performed for about 1 week-about 2 months while changing the medium, after which the culture is performed while aerating and stirring where necessary until formation of a cell sheet. Cells constituting the cell sheet obtained by such culture are maintained as retinal pigment epithelial cells. Maintenance of the cells as retinal pigment epithelial cells can be confirmed by detecting BEST1, RPE65, MERTK, CRALBP or the like as a specific differentiation marker.

Since the cell sheet formed in step (1) is adhered to collagen gel, for example, when it is directly used for transplantation and the like, the collagen gel is feared to prevent engraftment in a transplant recipient. In addition, it is feared that collagen gel may prevent binding and adhesion of a vascular forming cell layer and a retinal pigment epithelial cell layer. If the collagen gel can be removed in advance, it is conducible to the solution of such problem. In step (2) of the present invention, the collagen gel adhering to the cell sheet formed in step (1) is decomposed by collagenase. Those of ordinary skill in the art can select appropriate collagenase according to the kind of the collagen used for preparing the collagen gel. While the collagenase to be used for the decomposition of the collagen gel is not particularly limited as long as it has an activity to digest collagen gel, one that does not easily decompose collagen constituting the human basement membrane (e.g., Type-IV collagen etc.) is preferable. For example, collagenase derived from a microorganism induced from *Clostridium* (*Clostridium histolyticum*) or *Streptomyces* (*Streptomyces parvulus*), which are available at a commercial level, safe and have a high enzyme activity, can be used.

As the activity of the above-mentioned collagenase, the specific activity relative to the collagen weight in the collagen gel is important rather than the activity per unit weight of collagenase and the activity per unit volume of an aqueous collagenase solution. The specific activity of the collagenase to be used for dissolving collagen gel (collagenase activity/collagen weight) is preferably not less than 0.1 U/mg. When the specific activity of the collagenase is less than 0.1 U/mg, dissolution of the collagen gel may unpreferably take too long or the gel may unpreferably be dissolved insufficiently. It is more preferably within the range of 0.1-10,000 U/mg, further preferably 1-3,000 U/mg.

In the collagen method, a method of acting collagenase on collagen gel is not particularly limited. A collagenase solution prepared using, as a solvent, a medium or an isotonic solution having a buffering capacity may be added to a medium, or a cell-attached collagen gel detached from a cell culture dish may be immersed in the aforementioned collagenase solution. Since a transwell is used as a cell culture substratum in the present invention, a collagen gel layer can be exposed by recovering an insert and removing the membrane on the bottom of the insert, and the exposed collagen gel is preferably immersed directly in the above-mentioned collagenase solution.

In the collagen method, the time of dissolving the collagen gel by collagenase is not particularly limited. When the time of acting the collagenase is too long, cell functions such as adhesion ability, proliferative capacity and the like may unpreferably decomposed. While the time of dissolution by collagenase is subject to change due to specific activity of collagenase, temperature, the shape of collagen gel, collagenase treatment method and the like, it is generally 15 min-60 min. The collagenase treatment may be a single treatment or performed plural times.

The temperature during the treatment of collagen gel by collagenase in the collagen method is preferably set within the range of 10-42° C., more preferably 30-40° C., further preferably 36-38° C., since flowability of the cytoplasm of the cell generally decreases and the metabolic capacity decreases when the temperature inside living organisms becomes lower by not less than 10° C. (about 30° C. in human), the protein is denatured and the cell function decreases when the temperature exceeds 42° C., and the optimal temperature of collagenase is mostly 37° C. and a temperature below this level prolongs the dissolution time.

In the collagen method, when the dissolution of collagen gel proceeds, the cell sheet is gradually detached from the gel, and finally liberated in the collagenase solution. To recover the cell sheet, the cell sheet may be mechanically detached from the remaining gel, or may be recovered after complete dissolution of the gel. While the mechanical detachment shortens the time until recovery of the cell sheet, since the cell sheet may be destroyed, it is preferably recovered after complete dissolution of the gel.

While the cell sheet recovered as mentioned above can be directly used for the laminating step with a vascular forming cell layer, since the residual collagenase may inhibit adhesiveness to the vascular forming cell layer, it is preferably washed with a medium or an isotonic solution having a buffering capacity. The temperature during cleansing can be determined according to the collagen gel dissolution treatment by collagenase. To sufficiently remove residual collagenase, the sheet is preferably washed one or more times with a medium or an isotonic solution having a buffering capacity.

In the cell sheet composed of retinal pigment epithelial cells obtained by the collagen method, cytokine specific to a retinal pigment epithelial cell is secreted with the polarity similar to that in living organisms, and transepithelial electric resistance (TER) to be an index of close adhesionic bond between cells elevated as in living organisms. Therefore, it has a cell layer barrier function similar to that in living organisms. According to the collagen method, a cell sheet composed of retinal pigment epithelial cells and having functions similar to those in living organisms can be obtained.

In the cell sheet obtained by the collagen method, a tight junction is form between retinal pigment epithelial cells, and a basement membrane is formed on a contact surface with the collagen gel. In the present specification, the "basement membrane" is a membrane formed from the components produced from retinal pigment epithelial cells, and means a membrane containing at least a part of the basement membrane component (hereinafter to be referred to as a "basement membrane of m retinal pigment epithelial cells"). The basement membrane of the retinal pigment epithelial cell in living organisms is present as a thin film between a retinal pigment epithelial cell layer and an inner collagen layer constituting the Bruch's membrane, and is an extracellular matrix having Type-IV collagen, laminin, heparan sulfate proteoglycan (perlecan), nidogen and the like as representative components. The Bruch's membrane is a thin film between the retinal pigment epithelial cell layer and choroid, and has a 5-layer structure of a basement membrane of retinal pigment epithelial cells, an inner collagen layer, an elastin layer, an outer collagen layer, and a basement membrane of capillary lamina of choroid. A cell sheet composed of retinal pigment epithelial cells obtained by the collagen method contains a part (basement membrane of retinal pigment epithelial cell) of the structure of the Bruch's membrane. The formation of tight junction can be confirmed by observing hexagonally-shaped closely-adhered cell form, and expression of occludin, ZO-1 and the like between cells by immunostaining. The formation of basement membrane can be confirmed by observing expression of basement membrane markers such as laminin, heparan sulfate proteoglycan (perlecan), nidogen, or Type-IV collagen and the like on a cell surface by immunostaining, or observation with a scanning electron microscope.

Generally, retinal pigment epithelial cells cultured on a culture dish produce basement membrane components, but it is extremely difficult to detach the cells in the form of a usable retinal pigment epithelial cell sheet detached from a culture dish (Invest. Ophthalmol. Vis. Sci., 36(2), 1995, 381-390). According to the collagen method, retinal pigment epithelial cells together with a basement membrane produced from retinal pigment epithelial cells can be recovered as a sheet without utilizing an artificial membrane. Since retinal pigment epithelial cells form a monolayer structure, when they are handled singly, the sheet structure is disintegrated and the cells are scattered into cell units. Thus, transplantation thereof as a sheet is extremely difficult. On the other hand, since a cell sheet composed of retinal pigment epithelial cells obtained by the collagen method accompanies a basement membrane and has sufficient stiffness, it is not easily wrinkled during recovery, which makes the handling thereof extremely easy. Consequently, since laminating operation of vascular forming cell layers can be performed smoothly, and mounting on a cell transplantation device and a transplantation operation can be performed smoothly, cell transplantation can be performed with minimum invasion, and both the effect and the prognosis are expected to be improved. In addition, since a cell sheet composed of retinal pigment epithelial cells obtained by the collagen method accompanies a basement membrane, it is extremely advantageous for transplantation in a disease wherein the basement membrane is simultaneously disordered. For example, age-related macular degeneration sometimes accompanies disorder of Bruch's membrane. When a retinal pigment epithelial cell sheet obtained by the collagen method is used as a retinal pigment epithelial cell layer in the above-mentioned production method of the present invention, a basement membrane of the cell sheet produced by the method compensates for the disordered part, whereby the engrafting rate of the cell sheet can be improved, and a treatment effect thereof can also be expected. Hence, in the production method of the present invention, when a retinal pigment epithelial cell sheet obtained by the collagen method is used as a retinal pigment epithelial cell layer, the produced cell sheet is preferable as a sheet for transplantation recipienting a disease with a disordered basement membrane, and can be preferably utilized as a sheet for transplantation particularly targeting age-related macular degeneration.

The collagen method may further contain the following step (3):
(3) confirming the presence or absence of a basement membrane on the contact surface between the detached cell sheet and the collagen gel.

In step (3), formation of a cell sheet having a cell layer composed of retinal pigment epithelial cells and a basement membrane can be determined by confirming the presence or absence of the basement membrane of the cell sheet. The presence or absence of the basement membrane can be confirmed by a method similar to the aforementioned confirmation of the formation of the basement membrane, for example, expression of a basement membrane marker, observation with a scanning electron microscope and the like. For detection of the basement membrane, expression of a basement membrane marker may be confirmed at any site of the cell (e.g., cytoplasm, cellular membrane, nuclear membrane and the like). Preferably, a marker expressed on a contact surface with collagen gel is targeted.

The basement membrane marker in the present specification includes a transcription product, a translation product or a decomposition product of a gene specifically expressed in the basement membrane. Examples of such gene include laminin, heparan sulfate proteoglycan (perlecan), nidogen, Type-IV collagen and the like. Of these, laminin, Type-IV collagen and the like, which are main components of the basement membrane, are preferably used.

A sample to be used for "confirming the presence or absence of a basement membrane on the contact surface between the detached cell sheet and the collagen gel" is not particularly limited as long as it contains a basement membrane marker (e.g., RNA, protein, decomposition product thereof and the like) derived from the cell sheet (or cell) detached in step (2).

The expression of the basement membrane marker gene when the above-mentioned sample is RNA can be examined by preparing an RNA (e.g., total RNA, mRNA) fraction from the cell of the cell sheet detached in step (2) and detecting a transcription product of the marker gene contained in the fraction, or directly detecting a marker gene product in the cell without extracting RNA from the cell.

When an RNA (e.g., total RNA, mRNA) fraction is prepared from the cell, it can be prepared using a known method such as guanidine-CsCl ultracentrifugation method, AGPC method and the like. Using a commercially available RNA extraction kit (e.g., RNeasy Mini Kit; manufactured by QIAGEN etc.), total RNA with high purity can be prepared rapidly and conveniently from a trace amount of a sample. Examples of the method for detecting a transcription product of a basement membrane marker gene in an RNA fraction include a method using hybridization (Northernblot, dot blot, DNA chip analysis etc.), a method using PCR (RT-PCR, competitive PCR, real-time PCR etc.) and the like. Quantitative PCR methods such as competitive PCR, real-time PCR and the like are preferable since expression variation of a basement membrane marker gene can be detected rapidly and conveniently from a trace amount of a sample, and DNA chip analysis is preferable since expression variation of plural marker genes can be collectively detected and quantification performance can also be also improved by selecting a detection method and the like.

When Northernblot or dot blot hybridization is employed, the basement membrane marker gene can be detected using a nucleic acid (probe) capable of hybridizing with a transcription product of the gene. Examples of such nucleic acid include nucleic acid capable of hybridizing with a transcription product of a basement membrane marker gene under high stringent conditions. Examples of the "high stringent conditions" include hybridization reaction at 45° C. in 6×SSC (sodium chloride/sodium citrate), followed by washing once or more at 65° C. in 0.2×SSC/0.1% SDS and the like. Those of ordinary skill in the art can easily adjust to a desired stringency by appropriately changing the salt concentration of a hybridization solution, temperature of hybridization reaction, probe concentration, probe length, number of mismatch, hybridization reaction time, salt concentration of washing, washing temperature and the like.

The nucleic acid may be DNA, RNA or DNA/RNA chimera, with preference given to DNA.

The nucleic acid to be used as a probe may be double stranded or single stranded. When double stranded, it may be double stranded DNA, double stranded RNA or DNA:RNA hybrid. When single stranded, an antisense strand can be used. While the length of the nucleic acid is not particularly limited as long as it can specifically hybridize with the target nucleic acid, it is, for example, not less than about 15 bases, preferably not less than about 30 bases. To enable detection and quantification of the target nucleic acid, the nucleic acid to be used as a probe is preferably labeled. Examples of the labeling agent include radioisotope, enzyme, fluorescent substance, luminescence substance and the like. Examples of the radioisotope include [$^{32}$P], [$^{3}$H], [$^{14}$C] and the like. As the enzyme, a stable enzyme having a high specific activity is preferable, for example, β-galactosidase, β-glucosidase, alkaline phosphatase, peroxidase, malic acid dehydrogenase and the like. Examples of the fluorescent substance include fluorescamine, fluorescein isothiocyanate and the like. Examples of the luminescence substance include luminol, luminol derivative, luciferin, lucigenin and the like. Furthermore, biotin-(strept)avidin can also be used for binding a probe and a label.

When Northern hybridization is employed, an RNA fraction prepared as mentioned above is separated by gel electrophoresis, transferred to a membrane of nitrocellulose, nylon, polyvinylidene difluoride and the like, hybridized under the above-mentioned "high stringent conditions" in a hybridization buffer containing a labeling probe prepared as mentioned above, and the amount of the label bound to the membrane is measured for each band by a suitable method, whereby the expression level of each basement membrane marker gene can be measured. Also in the case of dot blot, a membrane spotted with an RNA fraction is subjected to a similar hybridization reaction (performed for each marker gene), and the amount of the label at the spot is measured, whereby the expression level of each marker gene can be measured.

When DNA chip analysis is employed, for example, cDNA introduced with a suitable promoter such as T7 promoter and the like by a reverse transcription reaction is synthesized from an RNA fraction prepared as mentioned above, cRNA is synthesized using RNA polymerase (in this case, labeled cRNA is obtained by using a mononucleotide labeled with biotin and the like as a substrate). The labeled cRNA is contacted with a chip having the above-mentioned probe immobilized thereon to perform a hybridization reaction, and the amount of the label bound with each probe on the solid phase is measured, whereby the expression level of each basement membrane marker gene can be measured. This method is advantageous in terms of rapidness and convenience as the number of the detected differentiated marker genes (therefore, probes to be solid phased) increases.

On the other hand, when a marker gene is detected without extracting RNA from the cell, in situ hybridization can be used as the detection means. In this method, the cell is immobilized by treating the cell with a fixing agent, preferably a precipitation fixing agent, for example, acetone, or incubating the cell for a short time in a buffering formaldehyde solution, instead of extracting RNA from the cell. After imrecruitment, the cell is embedded in paraffin to form a block, and a slice cut out therefrom can be used as a sample. A well-prepared paraffin-embedded sample can be preserved at room temperature for many years. As nucleic acid to be used as a probe, those similar to the above-mentioned examples can be used. In situ hybridization is preferably used in the present invention since expression of a basement membrane marker on the contact surface between the cell and collagen gel can be directly confirmed.

Alternatively, expression of a basement membrane marker in the detached cell sheet in step (2) can be confirmed by preparing a protein fraction from the cell sheet (or cell), and detecting a translation product (i.e., marker protein) of the marker gene contained in the fraction, or directly detecting a translation product of the marker gene in the cell sheet (or cell), without extracting the protein from the cell sheet (or cell). A marker protein can be detected by an immunological measurement method (e.g., ELISA, FIA, RIA, Western blot etc.) using an antibody to each protein and, in the case of a protein showing a measurable physiological activity such as an enzyme and the like, it can be detected by measuring the physiological activity of each marker protein by a known method. Alternatively, a marker protein can also be detected by a mass spectrometry method such as MALDI-TOFMS and the like.

An antibody to each marker protein can be obtained according to a generally-used polyclonal antibody or monoclonal antibody production technique and using a marker protein or protein, or a partial peptide thereof as an immunization antigen.

When respective immunological measurement methods are applied to the present invention, setting of special conditions, operations and the like is not necessary. A measurement system of the basement membrane marker protein can be constructed by adding general technical consideration of those of ordinary skill in the art to general conditions and operation methods in each method. As for the detail of these general technical means, compendia, books and the like can be referred to. For example, "Radioimmunoassay" edited by Hiroshi Irie (Kodansha, published in 1974), "cont. Radioimmunoassay" edited by Hiroshi Irie (Kodansha, published in 1979), "Enzyme Immunoassay" edited by Eiji Ishikawa et al. (Igaku-Shoin, published in 1978), "Enzyme Immunoassay" edited by Eiji Ishikawa et al. (2nd edition) (Igaku-Shoin, published in 1982), "Enzyme Immunoassay" edited by Eiji Ishikawa et al. (3rd edition) (Igaku-Shoin, published in 1987), "Methods in ENZYMOLOGY", Vol. 70 (Immunochemical Techniques (Part A)), ibidem, Vol. 73 (Immunochemical Techniques (Part B)), ibidem, Vol. 74 (Immunochemical Techniques (Part C)), ibidem, Vol. 84 (Immunochemical Techniques (Part D: Selected Immunoassays)), ibidem, Vol. 92 (Immunochemical Techniques (Part E: Monoclonal Antibodies and General Immunoassay Methods)), ibidem, Vol. 121 (Immunochemical Techniques (Part I: Hybridoma Technology and Monoclonal Antibodies)) (all published by Academic Press) and the like can be referred to.

A vascular forming cell layer may be directly laminated on the aforementioned retinal pigment epithelial cell layer, or a vascular forming cell layer may be laminated via other layer. In the present invention, a retinal pigment epithelial cell layer and a vascular forming cell layer are preferably laminated directly.

The present invention also relates to a cell sheet comprising a retinal pigment epithelial cell layer and a vascular forming cell layer, obtained by the above-mentioned production method of the present invention. The cell sheet of the present invention preferably contains a cell layer formed from retinal pigment epithelial cells obtained by ex vivo differentiation induction of stem cells or progenitor cells and a vascular forming cell layer. When the retinal pigment epithelial cell layer is produced by the above-mentioned collagen method, the cell sheet of the present invention further contains basement membrane secreted from the retinal pigment epithelial cell layer. The cell sheet of the present invention is preferable as a transplantation material for the retinal treatment of patients with ophthalmic diseases. Examples of the ophthalmic disease include chorioretinal degeneration diseases such as age-related macular degeneration, retinitis pigmentosa, diabetic retinopathy, retinal detachment, central retinal artery occlusion, central retinal vein occlusion, chorioretinal atrophy, retinal pigment epithelial detachment, uveitis (Behcet's disease, Harada disease etc.), excessive myopia (pathologic myopia) and the like.

Since the cell sheet of the present invention contains a vascular forming cell layer, it can be transplanted with a high engraftment rate for a disease involving simultaneously disordered choroid. Therefore, the cell sheet obtained by the production method of the present invention is preferably used for the treatment of, among the chorioretinal degeneration diseases recited above as examples, particularly, ophthalmic diseases associated with chorioretinal atrophy, for which exclusive transplantation of retinal pigment epithelial cells could not afford a treatment effect with ease (age-related macular degeneration, retinitis pigmentosa, chorioretinal atrophy, retinal pigment epithelial detachment, uveitis (Behcet's disease, Harada disease etc.) and excessive myopia (pathologic myopia) etc.).

In addition, since the cell sheet of the present invention has a basement membrane made from components similar to those in living organisms, it can also be utilized for various screening purposes such as efficacy screening, toxicity evaluation and the like in the aforementioned ophthalmic diseases. For the efficacy screening for the aforementioned ophthalmic diseases, for example, the cell sheet of the present invention can be applied to screening for a substance having efficacy for the aforementioned ophthalmic diseases, according to the method described in JP-A-2007-500509. To be specific, the cell sheet of the present invention is cultured in the presence or absence of a candidate substance having efficacy under the stress conditions possibly causing the aforementioned ophthalmic diseases (e.g., light (e.g., white light, blue light; light induces death of retinal cells, particularly photoreceptor cells, and can be a macular degeneration inciting factor), A2E [retinoid N-retinylidene-N-retinyl-ethanolamine] (accumulation of A2E is considered to contribute to age-related neurodegeneration of retinal cells, particularly expression of macular degeneration), cigarette smoke aggregate (smoking is considered to be a risk factor of macular degeneration), external pressure (e.g., hydrostatic pressure; increase in the intraocular pressure is suspected to be involved in glaucoma)), and evaluation can be performed based on the number of photoreceptor that expresses rhodopsin, and by immunostaining using anti-caspase 3 antibody. For toxicity evaluation, the cell sheet of the present invention can be applied to screening for a toxic substance according to the method described in JP-A-2007-517210. To be specific, the cell sheet of the present invention is cultured in the presence or absence of a toxicity candidate substance and using the integrin marker peptide described in JP-A-2007-517210, excited with a laser at a wavelength of 488 nm, and the fluorescence at 520 nm is detected for evaluation. Moreover, the cell sheet of the present invention can also be utilized as an in-vitro model for the evaluation of various in vivo functions of retinal pigment epithelial cell such as the function relating to the maintenance of visual cells such as phagocytic capacity of photoreceptor outer segment, neuroprotective action and the like, retinal blood vessel barrier function such as pumping action, tight junction, and the like.

The cell sheet for transplantation of the present invention can be used for the treatment of the above-mentioned diseases in human and mammals other than human (e.g., monkey, mouse, rat, dog, bovine, horse, swine, sheep, goat, cat, rabbit, hamster, guinea pig etc.).

The range of the disease area to which the cell sheet for transplantation of the present invention can be applied is appropriately determined depending on the target disease, the animal species, age, sex, body weight and symptom of administration subject, and the like.

The cell sheet for transplantation of the present invention can be transplanted at once or in several portions. The application number of transplantation is determined by health-care professionals according to the disease and the guideline. For example, when the disease is age-related macular degeneration disease, the cell sheet for transplantation of the present invention may be transplanted two or more times depending on the severity thereof. When transplantation is performed plural times, the interval is not particularly limited, and a period of several days to several weeks may be placed.

The cell sheet for transplantation of the present invention is transplanted by health-care professionals according to an appropriate transplantation method in accordance with the guideline. When the cell sheet for transplantation of the present invention is transplanted under the retina, a transplantation method including delivering the sheet on a water flow from a punctured injection needle, up to the transplantation site under the retina of the eyeball, may be employed or a therapeutic apparatus exclusive for transplantation may also be used.

EXAMPLES

The present invention is explained in more detail in the following by referring to Examples, which are mere exemplifications and do not limit the scope of the present invention in any way.

Production Example 1

Preparation of Retinal Pigment Epithelial Cells

As the retinal pigment epithelial cells to be used in the following Production Example 2, used were mature retinal pigment epithelial cells (253G1, K11PD2, 59M8, 59SV2, 59SV3, 59SV9, 46a, K21EV15, 101EV3, K11EV9, 454E2) obtained by inducing differentiation of human iPS cell, and retinal pigment epithelial cells (hES, CMK6) obtained by inducing differentiation of ES cell, according to the method described in Neuroscience Letters 458 (2009) 126-131.
<Human iPS-Derived Retinal Pigment Epithelial Cells>

253G1 is a retinal pigment epithelial cell obtained by differentiation induction of human iPS cell (253G1) derived from healthy human as described in Nature Biotechnology 26, 101-106, 2008.

59SV2, 59SV3 and 59SV9 are retinal pigment epithelial cells obtained by inducing differentiation of human iPS cells derived from the same retinitis pigmentosa patient. The iPS cells were established by a method including introducing Oct3/4, Sox2, Klf4 and c-Myc into human skin-derived fibroblasts by using Sendai virus, according to the method described in Proc. Jpn. Acad., Ser. B 85 (2009) 348-362.

K21EV15, 101EV3, K11EV9 and 454E2 are retinal pigment epithelial cells obtained by inducing differentiation of human iPS cells derived from retinitis pigmentosa patients different from each other. The iPS cells were established by a method including introducing human Oct3/4, Sox2, Klf4, L-Myc and LIN28 into human skin-derived fibroblasts by using episomal vector, according to the method described in Nat Methods. 2011 May; 8 (5): 409-12).

<Monkey iPS-Derived Retinal Pigment Epithelial Cells>

46a is a retinal pigment epithelial cell obtained by inducing differentiation of monkey (cynomolgus monkey) iPS cell, according to the method described in Jpn. J. Transplant. 44 (2009) 231-235.

<ES-Derived Retinal Pigment Epithelial Cells> hES is a retinal pigment epithelial cell obtained by inducing differentiation of human ES cell line khES-1. CMK6 is a retinal pigment epithelial cell obtained by inducing differentiation of monkey ES cell, according to the method described in Neuroscience Letters 458 (2009) 126-131.

Production Example 2

Production Method of Retinal Pigment Epithelial Cell Sheet

<Preparation of Collagen Gel Mixed Solution>

The following SOLUTION A, SOLUTION B and SOLUTION C were prepared.
solution A: Swine tendon-derived acid-soluble Type-I collagen Cellmatrix I-A (Nitta Gelatin, 3.0 mg/ml),
solution B: concentrated culture medium at 5-fold concentration [DMEM/F12 (Invitrogen, 12500-062, 3 g) was dissolved in MilliQ water, and total volume (50 ml) was filter-treated], and
solution C: buffer for reconstitution
[1N NaOH (50 mM, 5 ml), NaHCO$_3$ (260 mM, 2.2 g) and HEPES (200 mM, 4.77 g) were dissolved in MilliQ water, and total volume (100 ml) was filter-treated]

Under cooling, solution B (2 vol) was mixed (pale-yellow) with solution A (7 vol) without bubbling. Then, solution C (1 vol) was added and the mixture was mixed (pale-pink) to give a 0.21% collagen gel mixed solution.

<Preparation of Retinal Pigment Epithelial Cell Sheet>

The 0.21% collagen gel mixed solution (200 μl) was added into the insert of a 12 mm transwell insert (0.4 μm Pore Polyester membrane; Corning, 3460), and the mixture was incubated at 37° C. for 30 min. Then, F10-10% FBS [F-10 (Sigma, N6908, 445 ml), FBS (50 ml), Penicilin-Streptomycin (Invitrogen, 15140-122, 5 ml)] was added by 1500 μl to the outside of the insert and 500 μl to the inside of the insert, and the transwell was incubated at 37° C. for 24 hr. Thereafter, the inside and outside of the insert were washed once with F10-10% FBS, the retinal pigment epithelial cells obtained in Production Example 1 were seeded to $5 \times 10^5$ cells (F10-10% FBS, 500 μl) inside the insert, and F10-10% FBS (1500 μl) was added to the outside of the insert. The retinal pigment epithelial cells were cultured in F10-10% FBS until confluence. After reaching confluent, the medium was changed to SFRM-B27 [DMEM (Sigma, D6046, 350 ml), F12 HAM (Sigma, N6658, 150 ml), B27 (Invitrogen, 17504-044, 10 ml), 200 mM L-Glutamine (Sigma, G7513, 5 ml), Penicilin-Streptomycin (Invitrogen, 15140-122, 5 ml), bFGF (wako, 060-04543, 10 ng/ml)] (1500 μl to the outside of the insert, 500 μl to the inside of the insert, medium change was 3 times/week), and the retinal pigment epithelial cells were cultured until they showed suitable color and shape.

<Cutting Out>

After progress for 6 weeks from the start of the culture, the membrane of the insert was removed, collagenase L (Nitta Gelatin, PBS(+): Sigma, 2600 U/ml, 100 μl) was added under the insert, and the insert was incubated at 37° C. for 60 min and washed 3 times with PBS(+). SFRM-B27 was added dropwise so that the retinal pigment epithelial cell sheet would not get dry and cut into a desired size with PALM MicroBeam (ZEISS).

<Property>

By immunohistochemistry of the tissue section, it was confirmed that the prepared cell sheet had a structure wherein a retinal pigment epithelial cell sheet, in which tight junction (ZO-1 positive) is formed, is undercoated by basement membrane (laminin, type-IV collagen positive), and type-I collagen used for sheet formation did not remain (type-I collagen negative).

Example 1

Production of Laminated Cell Sheet of Vascular Endothelial Progenitor Cell Layer and Retinal Pigment Epithelial Cell Layer <Preparation of Vascular Endothelial Progenitor Cell>

Using endothelial cell culture kit-2 (EGM-2 medium (containing 2% FBS); manufactured by Takara Bio, B3162), human vascular endothelial progenitor cells (ECFCs; manufactured by Takara Bio, PT056) were seeded at $1.3 \times 10^4$ cells/cm$^2$ in a temperature responsive culture dish (3.5 cm dish; manufactured by Cellseed, CS3007).

<Laminating of Vascular Endothelial Progenitor Cells on Retinal Pigment Epithelial Cell Sheet>

After lapse of 15 hr, the human iPS cell-derived retinal pigment epithelial cell sheet obtained in Production Example 1 was placed on the vascular endothelial progenitor cells in the temperature responsive culture dish. The medium was gently aspirated, and the cell sheet was arranged to be placed in the center of the temperature responsive culture dish. Thereafter, for preventing drying, 100 μl of EGM-2 medium at 20° C. was added, and the mixture was left standing for 30 min to convert the temperature-responsive polymer on the surface of the culture dish to be hydrophilic, whereby the cell sheet was detached.

The cell sheet was washed once with EGM-2 medium, and the obtained cell sheet was transferred to a culture dish for adherent cells (Lumox dish 35; manufactured by Greiner, 077331; bottom surface is removable by cutting with a scalpel). Using laser microdissection (PALM MicroBeam; manufactured by ZEISS), and the cell sheet was cut into a desired size to give a cell sheet wherein human vascular endothelial progenitor cells and human retinal pigment epithelial cells were laminated.

Example 2

Cell Sheet Transplantation

The laminated cell sheet obtained in Example 1 was subcutaneously transplanted to the latissimus dorsi muscle of NOD/SCID mouse. Tissue sections were prepared one week later. By immunohistochemistry using anti-CD31 antibody (endothelial cell), anti-HLA-1 antibody (transplanted human cell), and DAPI, engraftment of the transplanted cell sheet and formation of a vascular structure derived from the transplanted cells were observed (in FIG. 1, arrow "capillary (donor)"). From the results, it was confirmed that vascular endothelial progenitor cells matured into endothelial cells after transplantation, and could form a blood vessel.

Example 3

Cell Sheet Transplantation

The laminated cell sheet obtained in Example 1 is transplanted to the subretina of a rabbit with partially deleted retinal pigment epithelial cells and choroid. Tissue sections are prepared one week later. By immunohistochemistry using anti-CD31 antibody (endothelial cell), anti-HLA-1 antibody (transplanted human cell), and DAPI, engraftment of the transplanted cell sheet and vascular formation derived from the transplanted cells can be confirmed.

Comparative Example 1

The human retinal pigment epithelial cell sheet obtained in Production Example 2 (with no human vascular endothelial progenitor cell) is transplanted to the subretina of a rabbit with partially deleted retinal pigment epithelial cells and choroid. Tissue sections are prepared one week later. By immunohistochemistry using anti-CD31 antibody (endothelial cell), anti-HLA-1 antibody (transplanted human cell), and DAPI, it is found that the sheet structure is destroyed, a small number of the transplanted cells are detected in a dispersed manner and, as compared to Example, 3, a phenomenon of markedly decreased engrafting rate of the transplanted cells is observed.

Reference Example 1

Vascular Formation

Formation of vessels by vascular endothelial progenitor cells cultured in a medium containing VEGF was confirmed by the following method.
(Medium)
"EM": EGM-2 medium (containing 2% FBS; manufactured by Takara Bio, B3162)
"F10": F10-10% FBS (F-10 (Sigma, N6908) 445 ml, FBS 50 ml, Penicilin-Streptomycin (Invitrogen, 15140-122) 5 mL). The results obtained by using this medium as a vascular formation medium are shown as "F10" in FIG. 2.
"F10-1": The retinal pigment epithelial cell sheet produced in Production Example 2 was placed in the insert of a 12 mm transwell insert (0.4 µm Pore Polyester membrane; Corning, 3460), and F10-10% FBS was added into and outside the insert by 500 µl, 1500 µl, respectively. The cell sheet was cultured for one day, and the culture supernatant was recovered. The results obtained by using the culture supernatant as a vascular formation medium are shown as "F10-1" in FIG. 2.
"F10-2": The retinal pigment epithelial cell sheet produced in Production Example 2 was placed in the insert of a 12 mm transwell insert (0.4 µm Pore Polyester membrane; Corning, 3460), and F10-10% FBS was added into and outside the insert by 500 µl, 1500 µl, respectively. The cell sheet was cultured for 2 days, and the culture supernatant was recovered. The results obtained by using the culture supernatant as a vascular formation medium are shown as "F10-2" in FIG. 2.

(Vascular Formation)
Using the above-mentioned 4 kinds of media, human vascular endothelial progenitor cells (ECFCs; manufactured by Takara Bio, PT056) were seeded in each culture dish at $1.3 \times 10^4$ cells/cm$^2$. The cells were incubated at 37° C., 5% $CO_2$ and 4 hr later, the number of formed vasculars was counted under a microscope. The results of the number of formed vasculars obtain in 3 repeats of the experiment are shown in FIG. 2(A) for each medium used (*P<0.001; ANOVA, Scheffe test). Vascular formation could be morphologically confirmed for each of them by optical microscope photograph and fluorescence microscope photograph.

The concentration of VEGF in 4 kinds of media used was measured. As a result, EM was 1.44 ng/ml, F10 was 0 ng/ml, F10-1 was 2.64 ng/ml, and F10-2 was 2.80 ng/ml. F10 free of VEGF showed a markedly small number of vascular formation. The media other than F10 showed many vascular formation, which confirms that VEGF promotes vascular formation by vascular endothelial progenitor cells. Also, from the results, it could be confirmed that a vascular formation treatment can be applied to the form of a cell sheet wherein a vascular endothelial progenitor cell layer and a retinal pigment epithelial cell layer are laminated, since a culture supernatant of retinal pigment epithelial cells could promote vascular formation.

Reference Example 2

Use of Matrigel

By the same method as that in Reference Example 1 except that a matrigel-coated culture dish was used, 4 kinds of media were used to culture human vascular endothelial progenitor cells and the number of formed vasculars was counted. The results of the number of formed vasculars obtain in 3 repeats of the experiment are shown in FIG. 2(B) for each medium used (*P<0.01 **P<0.05; ANOVA, Scheffe test). Vascular formation could be morphologically confirmed for each of them by optical microscope photograph and fluorescence microscope photograph.

As compared to Reference Example 1, the vascular formation number was markedly improved in all media using matrigel. Particularly, F10 free of VEGF showed a markedly small number of vascular formation (Reference Example 1), but vascular formation was promoted by using matrigel. These results confirm that vascular formation can be promoted by utilizing matrigel, irrespective of the presence of VEGF.

Production Conditions of Retinal Pigment Epithelial Cell Sheet Reference Example 3

Production Method of Retinal Pigment Epithelial Cell Sheet (Kind of Collagen)

In the same manner as in Production Example 2 except that, in the step of producing a cell sheet using 253G1 (iPS-retinal pigment epithelial cells) in Production Example 2, (A) swine skin-derived Type-I collagen TE (special order product: mainly containing Type-I collagen, a small quantity of Type-III collagen, Nitta Gelatin, 5 mg/ml) was used as 0.35% collagen mixed solution/well, (B) swine tendon-derived Type-I collagen T-1002 (special order product: Type-I collagen, Nitta Gelatin, 5.1 mg/ml) was used as 0.35% collagen mixed solution/well, (C) FITC-labeled collagen I (Chondrex, 1 mg/ml) was used as 0.07% collagen mixed solution/well, (D) FITC-labeled collagen I (special order, Chondrex, 3 mg/ml) was used as 0.21% collagen mixed solution/well, (E) atelocollagen (KOKEN, 3 mg/ml) was used as 0.21% collagen mixed solution/well, and (F) permeability collagen membrane for cell culture (KOKEN) was used, respectively, instead of swine tendon-derived acid-soluble Type-I collagen Cellmatrix I-A (Nitta Gelatin, 3 mg/ml) as 0.21% collagen mixed solution/well, cell sheets were produced and cut out to give retinal pigment epithelial cell sheets.

The test results of Production Example 2 and the cases using each of the aforementioned collagens were compared and evaluated in terms of 4 items [1. gel strength; 2. cell adhesion; 3. cell proliferation; 4. safety]. As a result, (A) {1. inferior; 2. equivalent; 3. inferior; 4. good}, (B) {1. good (5.1 mg/ml); 2. equivalent; 3. inferior; 4. good}, (C) {1. inferior (1 mg/ml); 2. inferior; 3. unknown; 4. unknown}, (D) {1. equivalent (3 mg/ml); 2. equivalent; 3. inferior; 4. unknown}, (E) {1. equivalent (3 mg/ml); 2. inferior; 3. unknown; 4. good}, and (F) {was not lysed by collagenase, thus unusable}. As for the gel strength, a certain level of strength is required to enable growth of retinal pigment epithelial cells. From such aspect, particularly preferable kind and concentration of collagen were the swine tendon-derived acid-soluble Type-I collagen Cellmatrix I-A of Production Example 2 and (B) swine tendon-derived Type-I collagen T-1002 used at the above-mentioned concentration. When the substrate does not have a certain level of strength, retinal pigment epithelium does not grow and cannot be used for the present invention.

Reference Example 4

Production Method of Retinal Pigment Epithelial Cell Sheet (Collagen Amount)

In the same manner as in Production Example 2 except that, in the step of producing a cell sheet using 253G1 (iPS-retinal pigment epithelial cell) of Production Example 2, the amount of the collagen gel mixed solution to be used was changed to 100 µl or 300 µl from 200 µl, cell sheets were produced and cut out, whereby retinal pigment epithelial cell sheets were recovered.

As compared to Production. Example 2, when the amount of the collagen gel mixed solution used was 100 µl, a thin collagen gel layer was formed in the center part due to an influence of the surface tension caused by the small amount of the collagen gel mixed solution and, as the culture proceeded, the seeded retinal pigment epithelial cells directly contacted the bottom membrane with ease, which caused breakage of the retinal pigment epithelial cell sheet during an operation to cut out the sheet. When the amount of the collagen gel mixed solution used was 300 µl, since the amount of the collagen gel mixed solution was high, a thick collagen gel layer was formed, which relatively reduced the amount of the medium that could be retained in the insert, and therefore, maintenance culture was not easy to perform, collagenase treatment took time, and damages on the cell sheet were feared to become greater.

Reference Example 5

Production Method of Retinal Pigment Epithelial Cell Sheet (Amount of Collagenase and Treatment Time)

In the same manner as in Production Example 2 except that, in the step of producing a cell sheet using 253G1 (iPS-retinal pigment epithelial cell) of Production Example 2, 1% Collagenase L (Nitta Gelatin) or Type I collagenase (Roche) was contacted with the retinal pigment epithelial cell sheet for 10 min in an amount of 10 µl, 20 min in an amount of 10 µl, 30 min in an amount of 10 µl, 60 min in an amount of 10 µl, 20 min in an amount of 20 µl, 60 min in an amount of 20 µl, and 50 min in an amount of 30 µl, instead of 30 min in an amount of 30 µl, cell sheets were produced and cut out, whereby retinal pigment epithelial cell Sheets were recovered.

As a result, when a collagenase treatment was performed for 60 min in an amount of 10 µl or 60 min in an amount of 20 µl, collagen decomposition of the same level as with 30 µl for 30 min was observed.

Reference Example 6

Production Method of Retinal Pigment Epithelial Cell Sheet (Number of Seeded Cells)

In the same manner as in Production Example 2 except that, in the step of producing a cell sheet using 253G1 (iPS-retinal pigment epithelial cell) of Example 1, the number of the cells to be seeded inside the insert was changed to (A) $5\times10^4$ cells/500 µl, (B) $1\times10^5$/500 µl or (C) $1\times10^6$/500 µl from $5\times10^5$ cells/500 µl, cell sheets were produced and cut out, whereby retinal pigment epithelial cell sheets were recovered.

As compared to Production Example 2, (A) and (B) required a longer time to reach cell confluence due to the small number of cells, and (C) showed slow growth and also tended to require a longer time to reach cell confluence.

Reference Example 7

Basement Membrane Formed on Retinal Pigment Epithelial Cell Sheet

A cryo section (frozen section) was produced from the cell sheet produced from 253G1 (iPS-retinal pigment epithelial cell) in Production Example 2, and subjected to immunohistochemical staining. Formation of a tight junction was confirmed by the expression of ZO-1, and formation of a basement membrane was confirmed by the expression of laminin and Type-IV collagen. For detection of each protein, respective antibodies of rabbit anti-ZO-1 manufactured by Zymed (1:100 dilution), rabbit laminin manufactured by Abcam (1:200 dilution), and mouse anti-human collagen type IV antibody manufactured by Calbiochem (1:40) were used. Furthermore, the retinal pigment epithelial cell sheet was confirmed to have a monolayer epithelial form from the state of nuclear staining using 4',6-diamidino-2-phenylindole manufactured by Molecular Probes (DAPI; 1 µg/ml).

Evaluation of Retinal Pigment Epithelial Cell Sheet
Evaluation 1. Retinal Pigment Epithelial Specific Gene Expression Profile of Cell Sheet In the step of producing a cell sheet from 59SV3, 59SV9 (iPS-retinal pigment epithelial cells) in Production Example 2, the expression of BEST1, RPE65, MERTK, CRALBP in the cells constituting the sheets after lapse of 1 week, 4 weeks, 2 months, wherein the day when the medium was changed to SFRM-B27 after cell confluence was day 0, was confirmed by RT-PCR. As a result, expression of the same level as that of the positive control (human retinal pigment epithelial cell total RNA (manufactured by ScienCell, Cat NO. 6545)) was observed. Here, BEST1, RPE65, MERTK are genes specifically expressed in retinal pigment epithelial cells. CRALBP is a gene expressed in retinal pigment epithelial cells and Muller cells.

Evaluation 2. Measurement of Residual Collagen in Retinal Pigment Epithelial Sheet Cryo sections (frozen section) were produced by cutting out, before and after collagenase treatment, from respective cell sheets produced from 253G1 (iPS-retinal pigment epithelial cell) in Production Example 2, and subjected to immunohistochemical staining. The nucleus was stained with 4',6-diamidino-2-phenylindole (DAPI; 1 µg/ml) manufactured by Molecular Probes, and Collagen type 1 was stained with rabbit anti-human collagen type I antibody (1:40 dilution) manufactured by Calbiochem. As a result, collagen was not detected from the sheets after the collagenase treatment, and it was confirmed that collagenase removed collagen coated on the culture dish. On the other hand, collagen was detected from the sheets cut out before the collagenase treatment.

Evaluation 3. Cytokine Secretion Capability of Retinal Pigment Epithelial Cell Sheet The culture media on the Apical side and the Basal side in the transwell were recovered before the step of cutting out retinal pigment epithelial cell sheets from the cell sheets produced from 253G1 (iPS-retinal pigment epithelial cell) and 454E2 (iPS-retinal pigment epithelial cell) in Production Example 2, and the production amounts of VEGF and PEDF were detected by ELISA according to the method described in Arvydas M, IOVS. 2006; 47: 3612-3624. As a result, it was confirmed that, similar to the human embryo-derived retinal pigment epithelium reported in Arvydas M, IOVS. 2006; 47: 3612-3624, VEGF was mainly secreted on the Basal side, and PEDF was mainly secreted on the Apical side (FIG. 4). It was shown that the retinal pigment epithelial cell sheet produced from 253G1 and 454E2 in Production Example 2 has cytokine secretory capability similar to that in living organisms, and is superior in functionality.

Evaluation 4. Transepithelial Electric Resistance of Retinal Pigment Epithelial Cell Sheet A strong correlation is seen between the barrier function of a cell layer and impedance, namely, transepithelial/transendothelial electric resistance (TER). A probe was placed in the media inside and outside the insert according to the method described by MILLIPORE (using Millicell ERS-2), before the step of cutting out the retinal pigment epithelial cell sheet produced from 454E2 (iPS-retinal pigment epithelial cell) in Production Example 2, and TER was electrically measured. As a result, TER was 640 Ω·cm$^2$, and showed a high TER value like the human embryo-derived retinal pigment epithelium reported in Nature Protocols vol 4, No 5 662-673 (2009), FIG. 10. It was shown that the retinal pigment epithelial cell sheet of the present invention produced in Production Example 2 has a high barrier function similar to that in living organisms.

Evaluation 5. Transplantation of Retinal Pigment Epithelial Cell Sheet Derived from Monkey ES Cell A monkey retinal pigment epithelial cell sheet produced from monkey ES cell-derived retinal pigment epithelial cells, CMK6 in Production Example 2 was transplanted into one eye of a monkey according to the method described in Invest Ophthalmol Vis Sci. 1995 February; 36(2): 381-90. Before the transplantation, retinal photocoagulation was performed to disorder the retina of the eye to be subjected to transplantation. On day 28 from the transplantation into the one eye of the monkey having retinal photocoagulation macula formed therein, eye fundus photographs were taken, and images of the ocular fundus sections were produced as histological sections by using OCT (Optical coherence tomograph), based on which the condition of the retina was confirmed. As a result, no leakage of fluorescence was found by fluorescein angiography, the graft survived, and a disorder such as thinning of sensory retina and the like were not found.

Evaluation 6. Transplantation of Retinal Pigment Epithelial Cell Sheet Derived from Monkey iPS Cell A monkey retinal pigment epithelial cell sheet produced from monkey iPS cell-derived retinal pigment epithelial cells, 46a in Production Example 2 was transplanted under the retina of one eye for autologous transplantation and three eyes for cross transplantation according to the method described in Invest Ophthalmol Vis Sci. 1995 February; 36(2): 381-90. Up to one year post-transplantation, eye fundus photographs were taken, and images of the ocular fundus sections were produced as histological sections by using OCT (Optical coherence tomograph), based on which the condition of the retina was observed with the lapse of time. In cross transplantation, clear rejection reactions such as fibrous changes on the periphery of the graft, leakage of fluorescence by fluorescein angiography, and high brightness lesion under the retina by OCT were found. On the other hand, in autologous transplantation, such clear rejection was not observed, no leakage of fluorescence was found by fluorescein angiography, the graft survived, and a disorder such as thinning of sensory retina and the like were not found.

INDUSTRIAL APPLICABILITY

According to the present invention, it is possible to easily and stably produce a laminated sheet of retinal pigment epithelial cells, which has a vascular constituting cell layer capable of complementing a deficient choroidal blood vessel in the living body and supplying oxygen and nutrients to retina after transplantation. The cell sheet of the present invention is extremely useful, since it is superior in the engraftment rate and functionality, and can also treat severe chorioretinal degeneration diseases, for which simple retinal pigment epithelial cell transplantation cannot easily afford a sufficient treatment effect, such as chorioretinal degeneration diseases, particularly, high myopia and severe uveitis and the like, which are associated with chorioretinal atrophy.

The contents disclosed in any publication cited in the present specification, including patents and patent applications, are hereby incorporated in their entireties by reference, to the extent that they have been disclosed herein.

This application is based on a patent application No. 2012-185932 filed in Japan (filing date: Aug. 24, 2012), the contents of which are incorporated in full herein.

The invention claimed is:

1. A method of producing a cell sheet comprising a retinal pigment epithelial cell layer and a vascular forming cell layer with no vascular structure, comprising
   (1) a step of seeding and culturing retinal pigment epithelial cells on a swine tendon-derived fibrotic collagen gel to form the retinal pigment epithelial cell layer composed of the retinal pigment epithelial cells, wherein the concentration of collagen in the swine tendon-derived fibrotic collagen gel is 0.21-0.35%,
   (2) a step of decomposing the swine tendon-derived fibrotic collagen gel with collagenase to detach the retinal pigment epithelial cell layer composed of the retinal pigment epithelial cells, and
   (3) a step of laminating the retinal pigment epithelial cell layer and the vascular forming cell layer with no vascular structure by placing a sheet-like retinal pigment epithelial cell layer on a vascular forming cell layer with no vascular structure cultured in a culture container such that the vascular forming cell layer with no vascular structure contacts a basal surface of the retinal pigment epithelial cell layer, wherein a density of the vascular forming cell layer relative to the retinal pigment epithelial cell layer is $1\times10^2$–$1\times10^6$ cells/cm$^2$, thereby producing the cell sheet comprising the retinal pigment epithelial cell layer and the vascular forming cell layer with no vascular structure.

2. The production method according to claim 1, wherein the vascular forming cell layer is composed of at least one cell selected from the group consisting of hemangioblast, vascular endothelial progenitor cell, and vascular endothelial cell.

3. The production method according to claim 1, wherein the vascular forming cell layer is composed of a tissue or cell derived from a patient to be transplanted with the cell sheet, or a cell derived from a donor having an HLA type matched with the patient's HLA type.

4. The production method according to claim 1, wherein the retinal pigment epithelial cell is obtained by inducing differentiation of ES cell, iPS cell or progenitor cell.

5. The production method according to claim 2, wherein the retinal pigment epithelial cell is obtained by inducing differentiation of ES cell, iPS cell or progenitor cell.

6. The production method according to claim 2, wherein the vascular forming cell layer is composed of a tissue or cell derived from a patient to be transplanted with the cell sheet, or a cell derived from a donor having an HLA type matched with the patient's HLA type.

7. The production method according to claim 3, wherein the retinal pigment epithelial cell is obtained by inducing differentiation of ES cell, iPS cell or progenitor cell.

8. The production method according to claim 1, wherein the cell sheet reconstructs retinal tissue and choroid through vascular formation when transplanted.

* * * * *